United States Patent [19]

Naka et al.

[11] Patent Number: 5,439,905
[45] Date of Patent: Aug. 8, 1995

[54] THIENODIAZEPINE COMPOUNDS AND THEIR USE

[75] Inventors: Yoichi Naka, Iruma; Keiichiro Haga, Chikujo; Masahiro Hosoya, Iruma, all of Japan

[73] Assignee: Yoshitomi Pharmaceutical Industries, Ltd., Osaka, Japan

[21] Appl. No.: 66,130

[22] PCT Filed: Sep. 30, 1991

[86] PCT No.: PCT/JP91/01315

§ 371 Date: May 27, 1993

§ 102(e) Date: May 27, 1993

[87] PCT Pub. No.: WO93/07152

PCT Pub. Date: Apr. 15, 1993

[51] Int. Cl.$^6$ .............. A61K 31/55; C07D 487/04; C07D 495/00
[52] U.S. Cl. ................. 514/220; 540/494; 540/495; 540/449; 540/503; 514/219; 514/221
[58] Field of Search .............. 540/494, 495, 499, 503; 514/219, 220, 221

[56] References Cited

U.S. PATENT DOCUMENTS 4,992,437  2/1991  Naka et al. .................. 514/221

FOREIGN PATENT DOCUMENTS 0348523  1/1990  European Pat. Off. ........... 514/221
0434364  6/1991  European Pat. Off. ........... 514/222
91/223290 10/1991  Japan ........................ 514/221
3-223290 10/1991  Japan ........................ 514/221

*Primary Examiner*—Robert T. Bond
*Attorney, Agent, or Firm*—Wenderoth, Lind & Ponack

[57] ABSTRACT

Thienodiazepine compounds of the formula

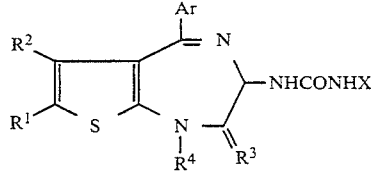

wherein each symbol is as defined in the specification, their pharmaceutically acceptable salts, and pharmaceutical compositions containing said compound.

Since the compounds possess excellent antagonistic actions on cholecystokinin and gastrin, and exhibit potent and durable suppressive actions on pancreatic enzyme secretion and gastric acid secretion, they are useful as medicaments acting on the central nervous system and the peripheral nervous system, as well as prophylactic and therapeutic medicines for pancreatic disorders and gastrointestinal ulcers. Furthermore, they are expected to exhibit anti-dementia actions based on their antagonistic actions on cholecystokinin, and are useful as an anti-dementia.

4 Claims, No Drawings

THIENODIAZEPINE COMPOUNDS AND THEIR USE

CROSS REFERENCE TO RELATED EARLIER APPLICATION

This application is a 371 of /JP91/10315 filed 30 Sep. 1991.

TECHNICAL FIELD

The present invention relates to novel thienodiazepine compounds having superior antagonistic action on cholecystokinin and gastrin, pharmaceutically acceptable salts thereof, and pharmaceutical use thereof.

BACKGROUND ART

International Publication No. WO 89/05812 discloses a thienodiazepine compound having an antagonistic action on cholecystokinin and gastrin.

Cholecystokinin (also referred to as CCK) is a neuropeptide consisting of 33 amino acids, and CCK-8 which consists of 8 amino acids at the C terminus also reveals activity. Gastrin consists of 34 amino acids, and pentagastrin which consists of 5 amino acids at the C terminus also shows activity. The amino acid sequence of pentagastrin is identical with that at the C terminus of CCK. Both exist in gastrointestinal tissues and the central nervous system, and are concerned with the control of pancreatic enzyme secretion and gastric acid secretion.

Since the substances which exhibit an antagonistic action on CCK and gastrin are effective in the prophylaxis and therapy of such diseases as pancreatic disorders and gastrointestinal ulcers, a number of such antagonistic substances have been studied so far. Also, it has recently been reported that the antagonistic action on CCK is related to an anti-dementia action.

As an antagonistic substance to CCK, benzotripto is known [Proc. Natl. Acad. Sci. U.S.A., vol. 78, p. 6304 (1981)], and proglumide is known as an antagonistic substance to gastrin [J. Med. Chem., vol. 27, p. 1597 (1984)]. Their actions are, however, relatively weak, and compounds having higher activities have been desired.

Besides, peptide antagonistic substances are not entirely satisfactory in that the durability of their actions is short and in that they are unstable and poorly absorbed.

DISCLOSURE OF THE INVENTION

The present inventors have conducted intensive studies with the aim of solving the above-mentioned problems, and found that a certain kind of thienodiazepine compound achieves the purpose, which resulted in the completion of the invention.

That is, the present invention relates to thienodiazepine compounds of the formula

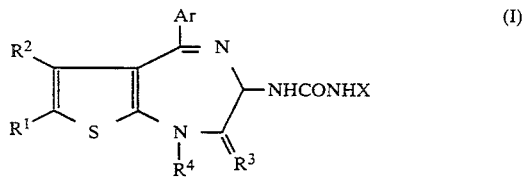

(I)

wherein $R^1$ and $R^2$ are the same or different and respectively stand for a hydrogen, a halogen, an alkyl or an aralkyl, or mean a group wherein $R^1$ and $R^2$ combined together form a ring; $R^3$ stands for an oxygen, $R^4$ stands for a hydrogen, an alkyl, an alkenyl or a group of the formula $-(CH_2)_m COOR^6$ (wherein $R^6$ stands for a hydrogen, an alkyl, an alkenyl or an aralkyl and m stands for an integer of 1-6), or $R^3$ and $R^4$ stand for a group wherein $R^3$ and $R^4$ combined together form a group of the formula $=N-N=C(R^5)-$ [wherein $R^5$ stands for a hydrogen, an alkyl, an alkenyl, an aralkyl or a group of the formula $-(CH_2)_n COOR^7$ (wherein $R^7$ stands for a hydrogen, an alkyl, an alkenyl or an aralkyl and n stands for an integer of 1-6]; and Ar and X are the same or different and respectively stand for an aryl, an aralkyl or a heteroaryl, and pharmaceutically acceptable salts thereof.

The present invention also relates to pharmaceutical compositions containing the above-mentioned compounds.

In the foregoing definition and the present specification, the halogen means chlorine, bromine, fluorine or iodine; the alkyl means an alkyl having 1 to 20 carbon atoms such as methyl, ethyl, propyl, isopropyl, butyl, isobutyl, tert-butyl, pentyl, isopentyl, tert-pentyl, hexyl, octyl, 2-ethylhexyl, 1,1,3,3-tetramethylbutyl, nonyl, decyl, dodecyl, tetradecyl, octadecyl or eicosyl; the alkenyl means an alkenyl having 2 to 8 carbon atoms such as vinyl, 1-propenyl, allyl, isopropenyl, 2-butenyl, 2-pentenyl, 3-hexenyl or 6-octenyl; the alkoxy means an alkoxy having 1 to 20 carbon atoms such as methoxy, ethoxy, propoxy, isopropoxy, butoxy, isobutoxy, tert-butoxy, pentyloxy, hexyloxy, octyloxy, decyloxy, dodecyloxy, octadecyloxy or eicosyloxy; the aralkyl means benzyl, 1-phenylethyl, 2-phenylethyl, 3-phenylpropyl, 4-phenylbutyl, 1-naphthylmethyl, 2-naphthylmethyl or diphenylmethyl which may have, on the aromatic ring, 1 to 3 substituents selected from among halogen, alkyl, alkoxy, trifluoromethyl, nitro, amino, cyano and hydroxyl group; the aryl means phenyl, 1-naphthyl, 2-naphthyl or the like which may have, on the aromatic ring, 1 to 3 substituents selected from among halogen, alkyl, alkoxy, trifluoromethyl, nitro, amino, cyano and hydroxyl group; the heteroaryl means pyridyl (2-pyridyl, 3-pyridyl, 4-pyridyl), quinolyl (2-quinolyl, 3-quinolyl), indolyl (2-indolyl, 3-indolyl), thienyl (2-thienyl, 3-thienyl), furyl (2-furyl, 3-furyl), benzofuranyl (2-benzofuranyl, 3-benzofuranyl), 1H-benzimidazol-2-yl, 2-benzothiazolyl or the like which may have, on the ring, 1 to 3 substituents selected from among halogen, alkyl, alkoxy, trifluoromethyl, nitro, amino, cyano and hydroxyl group; and the ring formed combinedly together by $R^1$ and $R^2$ means cyclopentene ring, cyclopentadiene ring, cyclohexene ring, cyclohexadiene ring, benzene ring, cycloheptene ring, cycloheptadiene ring, cycloheptatriene, or the like.

As the pharmaceutically acceptable salts of the compounds of the formula (I), exemplified are acid addition salts with inorganic acids or organic acids and salts with inorganic bases, organic bases or amino acids. From the purposes of the present invention, substantially non-toxic salts are preferable.

Since the compounds of the formula (I) have at least one chiral carbon atom, they can exist as a racemate, an optically active isomer or a diastereomer, all of which are encompassed in the present invention.

The compounds of the formula (I) of the present invention can be produced by condensing a compound of the formula

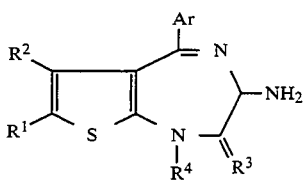

wherein each symbol is as defined above, with an isocyanate of the formula

X—NCO    (III)

wherein X is as defined above.

The condensation of a compound of the formula (II) and a compound of the formula (III) is carried out in a suitable solvent which does not adversely affect the reaction. The solvent is exemplified by an organic solvent such as tetrahydrofuran, diethyl ether, diisopropyl ether, dioxane, dichloromethane, chloroform, ethyl acetate, benzene, toluene, xylene, dimethylformamide or dimethylacetamide.

While the temperature of the condensation varies depending on the reagent and solvent to be used, it is preferably between $-20°$ C. and the boiling point of the solvent used.

The compounds of the formula (I) wherein $R^3$ and $R^4$ combined form a group of the formula $=N-N=C(R^5)-$ can be produced by reacting a compound (I) wherein $R^3$ is an oxygen and $R^4$ is a hydrogen which is represented by the formula

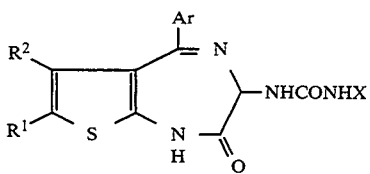

wherein each symbol is as defined above, with a thionation reagent to obtain a compound of the formula

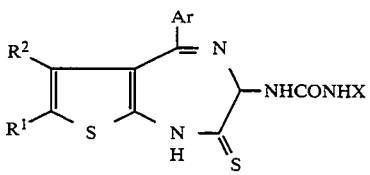

wherein each symbol is as defined above, followed by the reaction of this compound of the formula (V) with a compound of the formula $R^5CONHNH_2$    (VI)

wherein $R^5$ is as defined above, or alternatively by the reaction of the compound of the formula (V) with hydrazine hydrate to obtain a compound of the formula

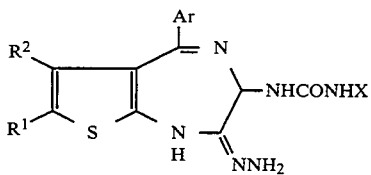

wherein each symbol is as defined above, followed by the reaction of the compound (VII) with a compound of the formula $R^5COOH$    (VIII)

wherein $R^5$ is as defined above, or its reactive derivative or with a compound of the formula $R^5C(OR^8)_3$    (IX)

wherein $R^8$ stands for an alkyl such as methyl or ethyl and $R^5$ is as defined above.

As the thionation reagent to be used for the above-mentioned method, exemplified are phosphorus pentasulfide, Lowesson reagent [2,4-bis(4-methoxyphenyl)-1,3,2,4-diphosphetane-2,4-disulfide], and the like. As the reactive derivatives of the compounds of the formula (VIII), exemplified are acid halides, acid anhydrides, mixed acid anhydrides, $C_1-C_5$ alkyl esters, benzylesters, and the like.

The reaction of the compound of the formula (IV) with a thionation reagent usually proceeds in a solvent inert to the reaction (pyridine, dimethylaniline, benzene, toluene, xylene, tetrahydrofuran, chloroform, dioxane, etc. or a mixed solvent thereof) at a temperature ranging from 30° C. to 100° C. for 30 minutes to 5 hours.

The reaction of the compound of the formula (V) with the compound of the formula (VI) usually proceeds in a solvent inert to the reaction (benzene, toluene, xylene, tetrahydrofuran, dioxane, etc. or a mixed solvent thereof) in the presence of an organic acid (acetic acid, propionic acid, etc.), an inorganic acid (hydrochloric acid, sulfuric acid, etc.) or silica gel at a temperature ranging from room temperature to the refluxing temperature of the solvent used, for 30 minutes to 5 hours. The reaction of the compound of the formula (V) with hydrazine hydrate usually proceeds in a solvent inert to the reaction (methanol, ethanol, propanol, isopropyl alcohol, butanol, etc.) at a temperature ranging from 0° C. to 40° C. for about 5 minutes to about 3 hours.

The reaction of the compound of the formula (VII) with the compound of the formula (VIII) or its reactive derivative or the compound of the formula (IX) proceeds in a solvent inert to the reaction (benzene, toluene, xylene, tetrahydrofuran, dioxane, etc. or a mixed solvent thereof) in the presence of an organic acid (acetic acid, propionic acid, etc.), an inorganic acid (hydrochloric acid, sulfuric acid, etc.) or silica gel at a temperature ranging from room temperature to the refluxing temperature of the solvent used, for 30 minutes to 6 hours.

The thus-obtained compounds of the formula (I) can be separated from the reaction mixture and purified by the methods known per se such as recrystallization and chromatography.

The compounds of the formula (I) can be converted into their salts by the treatment with an inorganic acid (hydrochloric acid, hydrobromic acid, sulfuric acid, phosphoric acid, nitric acid, etc.), an organic acid (acetic acid, propionic acid, succinic acid, glycolic acid, lactic acid, malic acid, tartaric acid, citric acid, maleic acid, fumaric acid, methanesulfonic acid, ascorbic acid, etc.), an inorganic base (sodium hydroxide, potassium hydroxide, calcium hydroxide, magnesium hydroxide, zinc hydroxide, ammonium hydroxide, etc.), an organic base (methylamine, diethylamine, triethylamine, dicyclohexylamine, triethanolamine, ethylenediamine, trishydroxymethylaminomethane, quinine, guanidine, cinchonine, etc.) or an amino acid (lysine, ornithine, arginine, alanine, etc.).

Among the compounds of the present invention, those having a chiral carbon are usually obtained as racemates. The racemates can be resolved into their optical isomers. These optical isomers can be also produced by using optically active starting compounds. The individual diastereomers can be purified by fractional recrystallization or chromatography.

The compounds encompassed in the present invention are exemplified by the following.

Below, shown are the pharmacological actions of the compounds of the present invention.

The compounds of the present invention used for the test were as follows:

Compound A: 4-(2-chlorophenyl)-2-ethyl-8-methyl-6-(3-(3-methylphenyl)ureido)-8H-6,7-dihydro-thieno[3,2-f]-[1,4]diazepin-7-one Compound B: 4-(2-chlorophenyl)-2-ethyl-9-methyl-6-(3-(3-methylphenyl)ureido)-6H-thieno[3,2-f][1,2,4]-triazolo[4,3-a][1,4]diazepine As the control compounds, used were CCK-8, CCK-4 and the following compound.

L-364718: N-(2,3-dihydro-1-methyl-2-oxo-5-phenyl-1H-1,4- benzodiazepin-3-yl)-1H-indole-2-carboxamide

EXPERIMENT EXAMPLE 1

CCK Receptor-binding

The entire pancreas of a male mongrel adult dog was extracted and the fat tissues thereof were removed. The residual portion was homogenized in 50 mM Tris hydrochloride (pH 7.5) (Blinkman•Polytron PT20). After the filtration with nylon cloth (120 mesh) and subsequent centrifugation (50,000×g, 12 minutes), the obtained sediment was homogenized in a Tris buffer solution in the same manner as mentioned above and the homogenate was centrifuged. The obtained sediment was suspended in a buffer solution for binding assay (5 mM magnesium chloride, 5 mM dithiothreitol, 2 mg/ml bovine serum albumin, 0.1 mg/ml bacitracin, and 50 mM Tris hydrochloride, pH 7.2) containing 0.14 mg/ml trypsin-inhibitor (soy bean), and the suspension was used as a receptor source.

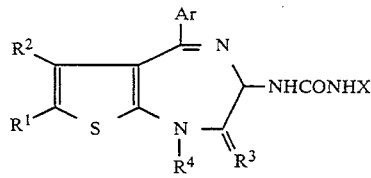

| No. | Ar | R¹ | R² | R³ | R⁴ | X | melting point (°C.) |
|---|---|---|---|---|---|---|---|
| 1 | 2-ClPh | Et | H | O | Me | 3-MePh | 226–227 |
| 2 | 2-ClPh | Et | H | =N—N=C(Me)— | | 3-MePh | 250–252 |
| 3 | 2-ClPh | Et | H | =N—N=C(Me)— | | 3-MePh | 6-(R) compound: 243–245 (decomposition) |
| 3 | 2-ClPh | Et | H | =N—N=C(Me)— | | 3-MePh | 6-(S) compound: 242–244 (decomposition) |
| 4 | 2-ClPh | Et | H | O | Me | 3-MeOPhCH₂— | |
| 5 | 2-ClPh | Et | H | O | Me | 2-MePh— | |
| 6 | 2-ClPh | Et | H | O | Me | 4-MePh— | |
| 7 | 2-ClPh | Et | H | O | Me | 3-ClPh— | |
| 8 | 2-ClPh | Et | H | O | Me | 3,4-(Cl)₂Ph— | |
| 9 | Ph | Et | H | O | Me | 3-MePh | |
| 10 | Ph | H | H | O | Me | 3-MePh | |
| 11 | 2-MePh | Et | H | O | Me | 3-MePh | |
| 12 | 4-MeOPh | Et | H | O | Me | 3-MePh | |
| 13 | 3-MePh | Et | H | O | Me | 3-MePh | |
| 14 | Ph | Me | Me | O | Me | 3-MePh | |
| 15 | Ph | —(CH₂)₄— | | O | Me | 3-MePh | |
| 16 | 4-MeOPh | Et | H | =N—N=C(Me)— | | 3-MePh | |
| 17 | 2-ClPh | Et | H | =N—N=CH— | | 3-MePh | |
| 18 | 2-ClPh | Me | Me | =N—N=C(Me)— | | 3-MePh | |
| 19 | Ph | Cl | H | =N—N=C(Me)— | | 3-MePh | |
| 20 | Ph | Et | H | O | CH₂COOH | 3-MePh | |
| 21 | 2-NO₂Ph | Et | H | =N—N=C(Me)— | | 3-MePh | |

(In Table, Cl means chlorine, Et means ethyl, Me means methyl, MeO means methoxy, NO₂ means nitro, and Ph means phenyl)

Since the compounds of the present invention and their pharmaceutically acceptable salts possess excellent antagonistic actions on cholecystokinin and gastrin, and exhibit potent and durable suppressive actions on pancreatic enzyme secretion and gastric acid secretion, they are useful as medicaments acting on the central nervous system and the peripheral nervous system, as well as prophylactic and therapeutic medicines for pancreatic disorders and gastrointestinal ulcers. Furthermore, the compounds of the present invention are expected to exhibit anti-dementia actions based on their antagonistic actions on cholecystokinin, and are useful as an anti-dementia.

The binding assay was conducted by adding 50 μl of buffer solution (for the entire binding), unlabeled CCK-8 sulfate (for non-specific binding) or test compound (for the measurement of binding-inhibitory capability of $^{125}$I-CCK) having the final concentration of 1 μM and 50 μl of $^{125}$I-CCK-8 (63–67 TBq/mmol, 40,000–50,000 cpm) to 450 μl of membrane suspension (containing 100 μl of protein), incubating the reaction mixture at 20° C. for 30 minutes, suction-filtering the mixture with glass fiber filter paper (Whatmann G/FB), washing three times with 2.5 ml per each tube of an ice-cooled Tris buffer solution immediately after the suction-filtration, and measuring the radio activity concentration on the filter paper.

The effect of the test compound on binding to CCK receptor was estimated by the concentration at which the specific binding was suppressed by 50% (IC$_{50}$, nM) based on the inhibitory rate calculated by the following formula.

$$\% \text{ inhibition} = 100 - \frac{\text{Binding when Compound added} - \text{Non-specific binding}}{\text{Entire binding} - \text{Non-specific binding}} \times 100$$

The results are shown in Table 1.

TABLE 1

| Test compound | CCK binding, pancreas | IC$_{50}$ (nM) brain |
| --- | --- | --- |
| A | 11 | 31 |
| B | 1.2 | 10 |
| L-364718 | 0.4 | 85 |
| CCK-8 | 0.4 | 0.5 |
| CCK-4 | 800 | 83 |

When the compounds of the present invention are used as medicaments, they are usually admixed with pharmaceutically acceptable additives such as carriers, excipients, diluents and solubilizing agents (lactose, corn starch, talc, kaolin, physiological saline, sterilized water, etc.) and safely administered to patients in the form of tablets (including sugar-coated tablets and film-coated tablets), capsules, powders, injections, transfusions, suppositories, cataplasms, or the like.

While the dosage varies depending on sex, age, body weight, symptom and so on of patients, the preferable daily dosage for oral administration is usually in the range of from about 1 to about 500 mg per adult.

The present invention is specifically explained by illustrating examples, to which the present invention is not limited.

EXAMPLE 1

6-Amino-4-(2-chlorophenyl)-2-ethyl-8-methyl-8H-6,7-dihydrothieno[3,2-f][1,4]diazepin-7-one (610 mg) was dissolved in 10 ml of tetrahydrofuran, and 277 mg of 3-methylphenyl isocyanate was added thereto. The mixture was kept standing for 30 minutes, and the solvent was distilled away under reduced pressure, followed by washing of the residue with diisopropyl ether. Ethyl acetate was added thereto, and the resulting crystals were filtered off. Recrystallization from chloroform-ethanol gave 470 mg of 4-(2-chlorophenyl)-2-ethyl-8-methyl-6-(3-(3-methylphenyl)ureido)-8H-6,7-dihydro-thieno[3,2-f][1,4]diazepin-7-one having a melting point of 226°–227° C..

EXAMPLE 2

In the same manner as in Example 1, 850 mg of 4-(2-chlorophenyl)-2-ethyl-9-methyl-6-(3-(3-methylphenyl)ureido)-6H-thieno[3,2-f][1,2,4]triazolo[4,3-a][1,4]diazepine having a melting point of 250°–252° C. was obtained from 1.04 g of 6-amino-4-(2-chlorophenyl)-2-ethyl-9-methyl-6H-thieno[3,2-f][1,2,4]-triazolo[4,3-a][1,4]diazepine and 3-methylphenyl isocyanate.

EXAMPLE 3

6-(R,S)-4-(2-Chlorophenyl)-2-ethyl-9-methyl-6-(3-(3-methylphenyl)ureido)-6H-thieno[3,2-f][1,2,4]triazolo[4,3-a][1,4]diazepine (1.12 g) was optically resolved by chromatography (hexane:dioxane:isopropyl alcohol=40:60:0.5) using an optically active column (Chirasphper, manufactured by Merck). The optical purity was determined by HPLC conducted under the similar conditions. Obtained were 380 mg of 6-(R) compound and 270 mg of 6-(S) compound.

| | optical purity (e.e. %) | optical rotation (0.5% methanol) | melting point |
| --- | --- | --- | --- |
| 6-(R) compound | >99.5 | +129.1 | amorphous |
| 6-(S) compound | >99.5 | −129.9 | 242–244° C. (ethanol) |

The absolute configuration was determined by X-ray structural analysis.

While the present invention has been described by the foregoing specification including examples, the embodiment described herein can be changed and modified in various manners within the scope and the spirit of the present invention.

What is claimed is:

1. A thienodiazepine compound of the formula

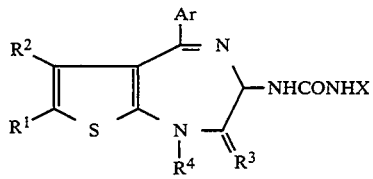

wherein

R$^1$ and R$^2$ are the same or different and respectively represent hydrogen, halogen, alkyl having 1 to 20 carbon atoms or benzyl, or R$^1$ and R$^2$ combined together with the carbon atoms to which they are attached form a ring selected from the group consisting of cyclopentene, cyclopentadiene, cyclohexene, cyclohexadiene, benzene, cycloheptene, cycloheptadiene and cycloheptatriene, R$^3$ and R$^4$ stand for a group wherein R$^3$ and R$^4$ combined together form a group of the formula =N—N=C(R$^5$)— wherein R$^5$ stands for hydrogen, alkyl having 1 to 20 carbon atoms, alkenyl having 2 to 8 carbon atoms, benzyl or a group of the formula —(CH$_2$)$_n$COOR$^7$ wherein R$^7$ stands for hydrogen, alkyl having 1 to 20 carbon atoms, alkenyl having 2 to 8 carbon atoms or benzyl and n stands for an integer of 1 to 6;

Ar stands for (1) phenyl which is unsubstituted or is substituted by 1 to 3 substituents selected from the group consisting of halogen, alkyl having 1 to 20 carbon atoms, alkoxy having 1 to 20 carbon atoms, trifluoromethyl, nitro, amino, cyano and hydroxyl, or (2) pyridyl which is unsubstituted or is substituted by 1 to 3 substituents selected from the group consisting of halogen, alkyl having 1 to 20 carbon atoms, alkoxy having 1 to 20 carbon atoms, trifluoromethyl, nitro, amino, cyano and hydroxyl; and X stands for (1) phenyl which is unsubstituted or is substituted by 1 to 3 substituents selected from the group consisting of halogen, alkyl having 1 to 20 carbon atoms, alkoxy having 1 to 20 carbon atoms, trifluoromethyl, nitro, amino, cyano and hydroxyl, or (2) pyridyl, quinolyl, indolyl, thienyl, furyl, benzofuranyl, 1H-benzimidazol-2-yl or 2-benzothiazolyl, each of which is unsubstituted or is substituted by 1 to 3 substituents selected from the group consisting of halogen, alkyl having 1 to 20 carbon atoms, alkoxy having 1 to 20 carbon atoms, trifluoromethyl, nitro, amino, cyano and hydroxyl;

or a pharmaceutically acceptable salt thereof.

2. A compound of claim 1, which is selected from the group consisting of 4-(2-chlorophenyl)-2-ethyl-9-methyl-6-(3-(3-methylphenyl)ureido)-6H-thieno[3,2-f][1,2,4]triazolo-[4,3-a][1,4]diazepine and 6-(S)-4-(2-chlorophenyl)-2-ethyl-9-methyl-6-(3-(3-methylphenyl)ureido)-6H-thieno[3,2-f][1,2,4]-triazolo[4,3-a][1,4]diazepine.

3. A pharmaceutical composition for prophylaxis and therapy of pancreatic disorders, gastrointestinal ulcers, and dementia which comprises a pharmaceutically effective amount of a thienodiazepine compound or pharmaceutically acceptable salt thereof as defined in claim 1 in combination with a pharmaceutically acceptable additive.

4. A method for preventing and treating pancreatic disorders, gastrointestinal ulcers, and dementia, which comprises administering to a patient in need of such treatment a pharmaceutically effective amount of a thienodiazepine compound or pharmaceutically acceptable salt thereof as defined in claim 1.

* * * * *